United States Patent
Conlon et al.

(10) Patent No.: US 8,535,239 B2
(45) Date of Patent: Sep. 17, 2013

(54) TISSUE HARVESTING DEVICE WITH MANUAL DICING MECHANISM

(75) Inventors: Sean P. Conlon, Loveland, OH (US); Joanne Hull, Cincinnati, OH (US); Wells D. Haberstich, Loveland, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 568 days.

(21) Appl. No.: 12/777,753

(22) Filed: May 11, 2010

(65) Prior Publication Data

US 2011/0282239 A1  Nov. 17, 2011

(51) Int. Cl.
A61B 10/00 (2006.01)
A61B 17/20 (2006.01)
A61B 17/50 (2006.01)
A61B 17/34 (2006.01)
A61N 1/30 (2006.01)

(52) U.S. Cl.
USPC .............. 600/564; 600/562; 604/19; 604/22; 606/132; 606/167; 606/184

(58) Field of Classification Search
USPC ............ 600/562, 564; 604/19, 22; 606/132, 606/167, 184
See application file for complete search history.

(56) References Cited

U.S. PATENT DOCUMENTS

| | | | |
|---|---|---|---|
| 5,329,846 A * | 7/1994 | Bonutti | 100/50 |
| 5,396,898 A * | 3/1995 | Bittmann et al. | 600/562 |
| 5,526,822 A | 6/1996 | Burbank et al. | |
| 5,575,293 A | 11/1996 | Miller et al. | |
| 5,694,951 A | 12/1997 | Bonutti | |
| 6,086,544 A | 7/2000 | Hibner et al. | |
| 6,990,982 B1 | 1/2006 | Bonutti | |
| 7,115,100 B2 | 10/2006 | McRury et al. | |
| 7,208,000 B2 * | 4/2007 | Love | 606/167 |
| 7,442,171 B2 | 10/2008 | Stephens et al. | |

(Continued)

FOREIGN PATENT DOCUMENTS

| EP | 1 514 521 | 3/2005 |
|---|---|---|
| EP | 2 022 407 | 2/2009 |
| WO | WO 2009/114868 | 9/2009 |

OTHER PUBLICATIONS

U.S. Appl. No. 12/483,305, filed Jun. 12, 2009, Hibner et al.

(Continued)

*Primary Examiner* — Sean Dougherty
*Assistant Examiner* — Devin Henson
(74) *Attorney, Agent, or Firm* — Frost Brown Todd LLC

(57) ABSTRACT

A dicing device dices tissue harvested from a patient. The dicing device comprises a grid cutting element and a tray to receive diced tissue. The dicing device may be integrated into an otherwise conventional biopsy device. The diced tissue specimens may be further processed, such as by being introduced into a self-expanding fistula plug creation and delivery system. The self-expanding fistula plug creation and delivery system comprises a sheet and a reinforcement tube. A scaffold material may be placed in the sheet, which may then be folded and reinforced, with the scaffold material being compressed in the sheet. The scaffold material may then be pushed into a catheter end. The catheter end may be inserted in a fistula. The scaffold material may then be flushed with a cell matrix that is based on the diced tissue to create a fistula plug, which may be left in the fistula.

17 Claims, 12 Drawing Sheets

(56) References Cited

U.S. PATENT DOCUMENTS

| | | |
|---|---|---|
| 7,611,473 B2 | 11/2009 | Boock et al. |
| 2004/0078090 A1 | 4/2004 | Binette et al. |
| 2004/0193071 A1 | 9/2004 | Binette et al. |
| 2005/0038520 A1 | 2/2005 | Binette et al. |
| 2005/0113736 A1 | 5/2005 | Orr et al. |
| 2005/0125077 A1 | 6/2005 | Harmon et al. |
| 2006/0271070 A1 | 11/2006 | Eriksson et al. |
| 2008/0071385 A1 | 3/2008 | Binette et al. |
| 2008/0103412 A1 | 5/2008 | Chin |
| 2008/0214955 A1 | 9/2008 | Speeg et al. |
| 2008/0234715 A1 | 9/2008 | Pesce et al. |
| 2008/0311219 A1 | 12/2008 | Gosiewska et al. |
| 2010/0160819 A1 | 6/2010 | Parihar et al. |

OTHER PUBLICATIONS

International Search Report and Written Opinion dated Oct. 14, 2011 for Application No. PCT/US2011/035921.

* cited by examiner

TISSUE HARVESTING DEVICE WITH MANUAL DICING MECHANISM

BACKGROUND

Fistulae can occur for a variety of reasons, such as, from a congenital defect, as a result of inflammatory bowel disease such as Crohn's disease, some sort of trauma, or as a side effect from a surgical procedure. Additionally, several different types of fistulae can occur in humans, for example, urethro-vaginal fistulae, vesico-vaginal fistulae, tracheo-esophageal fistulae, gastrointestinal fistulae, for example gastrocutaneous, enterocutaneous and colocutaneous fistulae, and any number of anorectal fistulae such as recto-vaginal fistula, recto-vesical fistulae, recto-urethral fistulae, and recto-prostatic fistulae. When fistulas form, they can track between intestinal segments or between an intestinal segment and other organs (e.g., bladder, vagina, etc.), adjacent tissue, or the skin. Fistulas are classified as internal when they communicate with adjacent organs (e.g., entero-enteric and rectovaginal fistulas, etc.) and external when they communicate with the dermal surface (e.g., enterocutaneous, peristomal and perianal fistulas, etc.).

Promoting and improving tissue healing around the fistula opening and in the fistula tract may be an important aspect of fistulae medical treatments. For instance, promoting and improving tissue healing may lead to quicker recovery times and lessen the opportunity for infection, particularly in a post-surgical context. Some advancements in the medical arts pertaining to systems, methods, and devices to promote and improve tissue healing in patients aim to add active biological components (e.g., tissue particles, stem cells, other types of cells, etc.) to a wound site (e.g., surgical site, accidental trauma site, etc.) or other defect site (e.g., caused by disease or other condition, etc.) to promote tissue regeneration or accelerate tissue healing. When adding biological components to a site, such components may be added independently or as part of a specifically designed matrix or other mixture depending on the condition being treated and goals of the treatment. Some examples of cell-based therapy technology are disclosed in U.S. Pub. No. 2008/0311219, entitled "Tissue Fragment Compositions for the Treatment of Incontinence," published Dec. 18, 2008, the disclosure of which is incorporated by reference herein. Additional examples of cell-based therapy technology are disclosed in U.S. Pub. No. 2004/0078090, entitled "Biocompatible Scaffolds with Tissue Fragments," published Apr. 22, 2004, the disclosure of which is incorporated by reference herein. Additional examples of cell-based therapy technology are disclosed in U.S. Pub. No. 2008/0071385, entitled "Conformable Tissue Repair Implant Capable of Injection Delivery," published Mar. 20, 2008, the disclosure of which is incorporated by reference herein.

Regardless of how the active biological components are delivered or applied to a site, the biological components must first be obtained and prepared. One approach for obtaining such biological components is to harvest the desired components from a healthy tissue specimen (e.g., in an adult human). Examples of devices and associated methods for collecting and processing harvested tissue are disclosed in U.S. Pub. No. 2004/0193071, entitled "Tissue Collection Device and Methods," published Sep. 30, 2004, the disclosure of which is incorporated by reference herein. Additional examples of devices and associated methods for collecting and processing harvested tissue are disclosed in U.S. Pub. No. 2005/0038520, entitled "Method and Apparatus for Resurfacing an Articular Surface," published Feb. 17, 2005, the disclosure of which is incorporated by reference herein. Additional examples of devices and associated methods for collecting and processing harvested tissue are disclosed in U.S. Pat. No. 7,611,473, entitled "Tissue Extraction and Maceration Device," issued Nov. 3, 2009, the disclosure of which is incorporated by reference herein. Additional examples of devices and associated methods for collecting and processing harvested tissue are disclosed in U.S. Pub. No. 2008/0234715, entitled "Tissue Extraction and Collection Device," published Sep. 25, 2008, the disclosure of which is incorporated by reference herein. Additional examples of devices and associated methods for processing harvested tissue are disclosed in U.S. Pub. No. 2005/0125077, entitled "Viable Tissue Repair Implants and Methods of Use," published Jun. 9, 2005, the disclosure of which is incorporated by reference herein. Additional examples of devices and associated methods for collecting and processing harvested tissue are disclosed in U.S. Pat. No. 5,694,951, entitled "Method for Tissue Removal and Transplantation," issued Dec. 9, 1997, the disclosure of which is incorporated by reference herein. Additional examples of devices and associated methods for collecting and processing harvested tissue are disclosed in U.S. Pat. No. 6,990,982, entitled "Method for Harvesting and Processing Cells from Tissue Fragments," issued Jan. 31, 2006, the disclosure of which is incorporated by reference herein. Additional examples of devices and associated methods for collecting and processing harvested tissue are disclosed in U.S. Pat. No. 7,115,100, entitled "Tissue Biopsy and Processing Device," issued Oct. 3, 2006, the disclosure of which is incorporated by reference herein.

Once harvested and suitably processed (e.g., incorporated with a scaffold, etc.), biological material such as tissue fragments may be applied to a wound site or other type of site within the human body in a variety of ways. Various methods and devices for applying such biological material are disclosed in one or more of the U.S. patent references cited above. Additional methods and devices for applying such biological material are disclosed in U.S. Pub. No. 2005/0113736, entitled "Arthroscopic Tissue Scaffold Delivery Device," published May 26, 2005, the disclosure of which is incorporated by reference herein.

While a variety of devices and techniques may exist for harvesting, processing, and applying biological components from a tissue specimen, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings. In the drawings, like numerals represent like elements throughout the several views.

Figure 1:
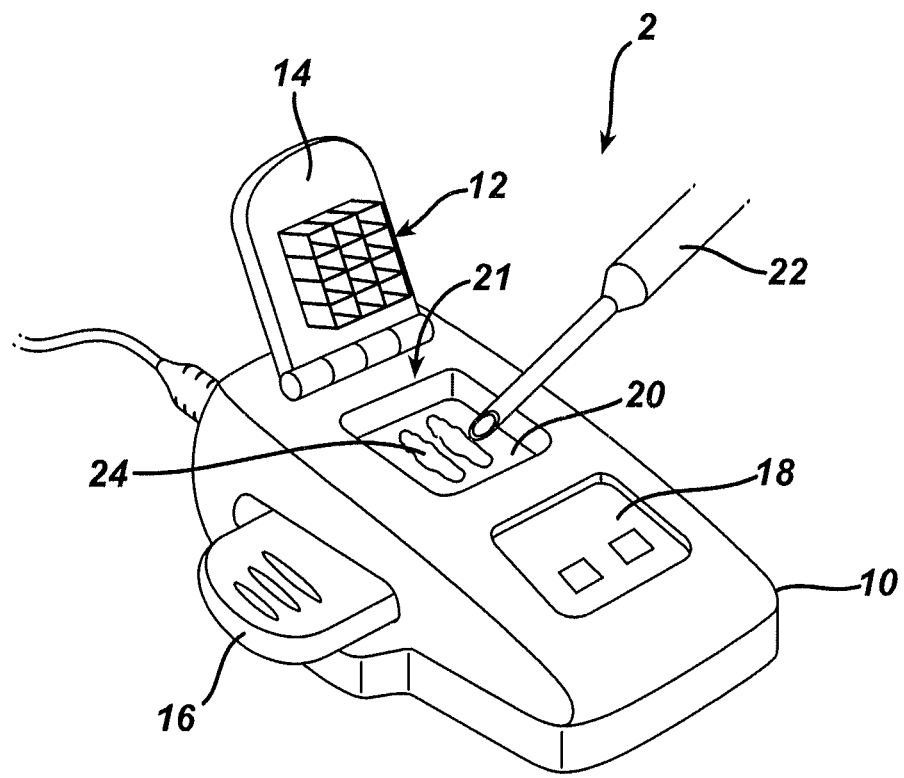
FIG. 1 depicts a perspective view of an exemplary version of a standalone tissue dicing device.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples should not be used to limit the scope of the present invention. Other features, aspects, and advantages of the versions disclosed herein will become apparent to those skilled in the art from the following description, which is by way of illustration, one of the best modes contemplated for carrying out the invention. As will be realized, the versions described herein are capable of other different and obvious aspects, all without departing from the invention. Accordingly, the drawings and descriptions should be regarded as illustrative in nature and not restrictive.

I. Overview of Exemplary Treatment Compositions, Devices, and Methods

Examples described herein include devices that are operable to harvest tissue, mince or morcellate tissue, and/or dispense a medical fluid at a target site in a patient. As described in greater detail below, the medical fluid may include any of a variety of biocompatible materials that accelerate tissue healing, promote tissue regeneration, and/or provide other results. As used herein, the terms "tissue treatment composition," "tissue repair composition," and "medical fluid" should be read interchangeably. It should also be understood that a tissue treatment composition or medical fluid as referred to herein may have any suitable consistency, including but not limited to the consistency of a slurry.

A medical fluid as referred to herein may be derived from any biocompatible material, including but not limited to synthetic or natural polymers. The consistency of the medical fluid may be viscous, or gel-like, that of a slurry composed of microparticles, or any other suitable consistency. By way of example only, any fluid consistency that may permit injection through a catheter may be used. The medical fluid may also provide adhesive characteristics, such that once it is injected at a target site (e.g., into a fistula), the fluid coagulates or gels (e.g., allowing for a plug to be retained within a fistula). The medical fluid of the present example is also able to support cell migration and proliferation such that healing at a target site in a patient can occur. The fluid is suitable to be mixed with biological materials. Examples of medical fluid components include but are not limited to thrombin, platelet poor plasma (PPP) platelet rich plasma (PRP), starch, chitosan, alginate, fibrin, polysaccharide, cellulose, collagen, gelatin-resorcin-formalin adhesive, oxidized cellulose, mussel-based adhesive, poly (amino acid), agarose, amylose, hyaluronan, polyhydroxybutyrate (PHB), hyaluronic acid, poly(vinyl pyrrolidone) (PVP), poly(vinyl alcohol) (PVA), polylactide (PLA), polyglycolide (PGA), polycaprolactone (PCL), and their copolymers, VICRYL® (Ethicon, Inc., Somerville, N.J.), MONOCRYL material, PANACRYL (Ethicon, Inc., Somerville, N.J.), and/or any other material suitable to be mixed with biological material and introduced to a wound or defect site, including combinations of materials. Other suitable compounds, materials, substances, etc., that may be used in a medical fluid will be apparent to those of ordinary skill in the art in view of the teachings herein.

By way of example only, one or more components in a medical fluid or tissue treatment composition may comprise at least one viable tissue fragment having one or more viable cells that, once applied, can proliferate and integrate with tissue at a target site in a patient. For instance, viable cells may migrate out of a tissue particle and populate a scaffold material, which may be positioned at a target site in a patient. Such tissue fragments may have been harvested from the same patient in whom they are reapplied; or may have been harvested from another person or source. The tissue fragments may comprise autogenic tissue, allogenic tissue, xenogenic tissue, mixtures of any of the foregoing, and/or any other type(s) of tissue. The tissue fragments may include, for example, one or more of the following tissues or tissue components: stem cells, cartilage tissue, meniscal tissue, ligament tissue, tendon tissue, skin tissue, muscle tissue (e.g., from the patient's thigh, etc.), periosteal tissue, pericardial tissue, synovial tissue, fat tissue, bone marrow, bladder tissue, umbilical tissue, embryonic tissue, vascular tissue, blood and combinations thereof. Of course, any other suitable type of tissue may be used, including any suitable combination of tissue types. In some versions, the type of tissue used is selected from a tissue type most resembling the tissue at, near, or surrounding the target site (e.g., fistula, etc.).

Tissue for providing at least one viable tissue fragment may be obtained using any of a variety of tissue biopsy devices or using other types of tissue harvesting devices or techniques. Exemplary biopsy devices include those taught in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pub. No. 2007/0118048, entitled "Remote Thumbwheel for a Surgical Biopsy Device," published May 24, 2007, and issued Oct. 28, 2008 as U.S. Pat. No. 7,442,171; U.S. Pub. No. 2008/0214955, entitled "Presentation of Biopsy Sample by Biopsy Device," published Sep. 4, 2008; U.S. Non-Provisional patent application Ser. No. 12/337,942, entitled "Biopsy Device with Central Thumbwheel," filed Dec. 18, 2008, and published Jun. 24, 2010 as U.S. Pub. no. 2010/0160819; and U.S. Non-Provisional patent application Ser. No. 12/483,305, entitled "Tetherless Biopsy Device with Reusable Portion," filed Jun. 12, 2009, and issued Jun. 26, 2012 as U.S. Pat. No. 8,206,316. The disclosure of each of the above-cited U.S. patents, U.S. patent application Publications, and U.S. Non-Provisional patent applications is incorporated by reference herein. Such biopsy devices may be used to extract a plurality of tissue specimens from one or more sites in a single patient. It should also be understood that any suitable device described in any other reference that is cited herein may be used to harvest tissue. Additional examples of devices that may be used to harvest tissue will be described in greater detail below. Other examples will be apparent to those of ordinary skill in the art in view of the teachings herein. Tissue harvesting sites may include the same sites in which tissue is reapplied as part of a treatment. In addition or in the alternative, tissue may be harvested from one site and then reapplied at some other site as part of a treatment. In some versions, the tissue is reapplied in the same patient from whom the tissue was originally harvested. In some other versions, the tissue is applied in a patient who is different from the patient from whom the tissue was originally harvested.

A tissue specimen may be obtained under aseptic conditions, and then processed under sterile conditions to create a suspension having at least one minced, or finely divided, tissue fragment. In other words, harvested tissue may be diced, minced or morcellated, and/or otherwise processed. Harvested tissue specimens may be minced and otherwise processed in any of a variety of ways. For instance, examples of tissue mincing and processing are described in U.S. Pub. No. 2004/0078090, the disclosure of which is incorporated by reference herein. Alternatively, merely exemplary non-conventional devices and techniques that may be used to mince and process tissue will be described in greater detail below, while other examples will be apparent to those of ordinary skill in the art in view of the teachings herein. In order to ensure viability of the tissue, agitators or other features of a mincing and/or mixing device may be designed to sever and mix (rather than crush or compress) the tissue. In some settings, tissue specimens may be minced and/or mixed in a standard cell culture medium, either in the presence or absence of serum. Tissue fragments may also be contacted with a matrix-digesting enzyme to facilitate cell migration out of an extracellular matrix surrounding the cells. Suitable matrix-digesting enzymes that may be used in some settings include, but are not limited to, collagenase, chondroitinase, trypsin, elastase, hyaluronidase, peptidase, thermolysin, and protease. The size of each tissue fragment may vary depending on the target location, method for delivering the treatment composition to the target site, and/or based on various other considerations. For example, the tissue fragment size may be chosen to enhance the ability of regenerative cells (e.g., fibroblasts) in the tissue fragments to migrate out of the tissue fragments, and/or to limit or prevent the destruction of cell integrity. In some settings, ideal tissue fragments are between approximately 200 microns and approximately 500 microns in size. As another merely illustrative example, ideal tissue fragments may be sized within the range of approximately 0.05 $mm^3$ and approximately 2 $mm^3$; or more particularly between approximately 0.05 $mm^3$ and approximately 1 $mm^3$. Of course, various other tissue fragment sizes may be ideal in various different settings.

In some versions, a medical fluid may comprise minced tissue fragments suspended in a biocompatible carrier. Suitable carriers may include, for example, a physiological buffer solution, a flowable gel solution, saline, and water. In the case of gel solutions, the tissue repair composition may be in a flowable gel form prior to delivery at the target site, or may form a gel and remain in place after delivery at the target site. Flowable gel solutions may comprise one or more gelling materials with or without added water, saline, or a physiological buffer solution. Suitable gelling materials include biological and synthetic materials. Exemplary gelling materials include the following: proteins such as collagen, collagen gel, elastin, thrombin, fibronectin, gelatin, fibrin, tropoelastin, polypeptides, laminin, proteoglycans, fibrin glue, fibrin clot, platelet rich plasma (PRP) clot, platelet poor plasma (PPP) clot, self-assembling peptide hydrogels, Matrigel or atelocollagen; polysaccharides such as pectin, cellulose, oxidized regenerated cellulose, chitin, chitosan, agarose, or hyaluronic acid; polynucleotides such as ribonucleic acids or deoxyribonucleic acids; other materials such as alginate, cross-linked alginate, poly(N-isopropylacrylamide), poly(oxyalkylene), copolymers of poly(ethylene oxide)-poly(propylene oxide), poly(vinyl alcohol), polyacrylate, or monostearoyl glycerol co-Succinate/polyethylene glycol (MGSA/PEG) copolymers; and combinations of any of the foregoing. In addition to providing a flowable carrier solution for tissue fragments, a gelling agent(s) may also act as an adhesive that anchors the tissue repair composition at the target site. In some versions, an additional adhesive anchoring agent may be included in the tissue repair composition or medical fluid. Also, one or more cross-linking agents may be used in conjunction with one or more gelling agents in order to cross-link the gelling agent.

The concentration of tissue fragments in a carrier and/or one or more medical fluid components may vary depending on the target site location, method for delivering the treatment composition to the target site, and/or for various other reasons. By way of example, the ratio of tissue fragments to carrier (by volume) may be in the range of about 2:1 to about 6:1, or in the range of about 2:1 to about 3:1. The medical fluid may also include one more additional healing agents, such as biological components that accelerate healing and/or tissue regeneration. Such biological components may include, for example, growth factors, proteins, peptides, antibodies, enzymes, platelets, glycoproteins, hormones, cytokines, glycosaminoglycans, nucleic acids, analgesics, viruses, isolated cells, or combinations thereof. The medical fluid may further include one or more additional treatment components that prevent infection, reduce inflammation, prevent or minimize adhesion formation, and/or suppress the immune system. In some versions where a scaffold is used in conjunction with a tissue treatment composition, one or more of these additional biological components or additional treatment components may be provided on and/or within the scaffold. Similarly, in some versions where a scaffold plug is used in conjunction with a tissue repair composition, one or more of these additional biological components or additional treatment components may be provided on and/or within the scaffold plug. Some examples described herein may also include one or more adhesive agents in conjunction with viable tissue fragments.

As noted above, the harvested tissue may be combined with a scaffold material and/or other substances as part of a medical fluid, as described herein, for administration to the patient. To the extent that tissue is incorporated with a scaffold material, it should be understood that any suitable material or combination of materials may be used to provide a scaffold. By way of example only, scaffold material may include a natural material, a synthetic material, a bioabsorbable polymer, a non-woven polymer, other types of polymers, and/or other types of materials or combinations of materials. Examples of suitable biocompatible materials include starch, chitosan, cellulose, agarose, amylose, lignin, hyaluronan, alginate, hyaluronic acid, fibrin glue, fibrin clot, collagen gel, gelatin-resorcin-formalin adhesive, platelet rich plasma (PRP) gel, platelet poor plasma (PPP) gel, Matrigel, Monostearoyl Glycerol co-Succinate (MGSA), Monostearoyl Glycerol co-Succinate/polyethylene glycol (MGSA/PEG) copolymers, laminin, elastin, proteoglycans, polyhydroxybutyrate (PHB), poly(vinyl pyrrolidone) (PVP), polylactide (PLA), polyglycolide (PGA), polycaprolactone (PCL), and their copolymers, non-woven VICRYL® (Ethicon, Inc., Somerville, N.J.), MONOCRYL material, fibrin, non-woven poly-L-lactide, and non-woven PANACRYL (Ethicon, Inc., Somerville, N.J.). Polymers may include aliphatic polyesters, poly(amino acids), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, poly(propylene fumarate), polyurethane, poly(ester urethane), poly(ether urethane), and blends and copolymers thereof. Suitable synthetic polymers for use in examples described herein may also include biosynthetic polymers based on sequences found in collagen, laminin, glycosaminoglycans, elastin, thrombin, fibronectin, starches, poly(amino acid), gelatin, alginate, pectin, fibrin, oxidized cellulose, chitin, chitosan, tropoelastin, hyaluronic acid, silk, ribonucleic acids, deoxyribonucleic acids, polypeptides, proteins, polysaccharides, polynucleotides, and combinations thereof. Other suitable materials or combinations of materials that may be used will be apparent to those of ordinary skill in the art in view of the teachings herein. It should also be understood that tissue mixed with a scaffold material may have any suitable particle size, and that the resulting mixture may at least initially have the consistency of a slurry or have any other suitable consistency. In some versions, the tissue particles include an effective amount of viable cells that can migrate out of the tissue particle and populate the scaffold. The term "viable," as used herein, should be understood to include a tissue sample having one or more viable cells.

In some versions, one or more components in a medical fluid or tissue treatment composition comprise one or more healing agents that promote tissue regeneration at a target site (e.g., within a fistula) and/or accelerate tissue healing at the target site. Healing agents may include any of a variety of biocompatible materials that accelerate tissue healing and/or promote tissue regeneration. Such biological components may include, for example, growth factors, proteins, peptides, antibodies, enzymes, platelets, glycoproteins, hormones, cytokines, glycosaminoglycans, nucleic acids, analgesics, viruses, isolated cells, or combinations thereof. The medical fluid may further include one or more additional treatment components that prevent infection, reduce inflammation, prevent or minimize adhesion formation, and/or suppress the immune system. In some versions where a scaffold is used in conjunction with a tissue treatment composition, one or more of these additional biological components or additional treatment components may be provided on and/or within the scaffold. Some examples described herein may also include one or more adhesive agents in conjunction with viable tissue fragments.

Examples described herein relate to the repair (e.g., closing) of lumens in a patient, such as anal fistulas and other types of fistulas. In particular, examples described herein include devices used in at least part of a process to create and/or deliver tissue repair compositions or medical fluid into a lumen such as an anal fistula. It should be understood that anal fistulas and/or other types of fistulas may be relatively difficult to repair (e.g., close) in some settings. The goal of a surgical repair of an anal fistula may be to close the fistula with as little impact as possible on the sphincter muscles. In some settings, a tissue repair composition or medical fluid as described herein may be delivered into the fistula as a liquid composition, a flowable gel or paste, a scaffold plug, or a combination of the two or more of the foregoing (e.g., a porous scaffold plug loaded with a medical fluid composition, etc). Anal fistulas may also be repaired by injecting bioresorbable fibrin glue into the fistula that seals the fistula and promotes tissue growth across the fistula in order to provide permanent closure. Various bioresorbable plugs may also be used to repair anal fistulas. The plug may comprise, for example, collagen protein, tissue, stem cells, and/or other medical fluid components referred to herein; and the plug may be inserted into the fistula where it promotes tissue growth across the fistula as the plug dissolves. If desired, the plug may be secured in place using one or more fasteners and/or one or more adhesive agents. As another merely illustrative example, a medical fluid may be introduced within the fistula, and the medical fluid may eventually harden and then dissolve and/or be absorbed.

Prior to applying a medical fluid to a fistula, it may be desirable in some settings to debride the wall of a fistula (e.g., to remove epithelial cells, etc.), otherwise agitate the wall of the fistula, and/or otherwise treat the walls of the fistula. While examples herein are discussed in the context of an anorectal fistula, it should be understood that the following exemplary devices and techniques may be readily applied to various other types of fistulae. Similarly, while the present example relates to treatment of a fistula in a patient, it should also be understood that the following exemplary devices and techniques may be readily applied with respect to various other types of conditions in a patient. Other suitable ways in which the devices and techniques described herein may be used will be apparent to those of ordinary skill in the art in view of the teachings herein.

As used herein, the term "fluid communication" (or in some contexts "communication") means that there is a path or route through which fluid (gas, liquid or other flowable material) may flow between two components, either directly or through one or more intermediate components. Similarly, the term "conduit" encompasses a conduit within or integrated with a valve. In other words, fluid communication between two components means that fluid can flow from one component to another but does not exclude an intermediate component (e.g., a valve, etc.) between the two recited components that are in fluid communication. Similarly, two or more components may be in mechanical "communication" with each other even if intermediate components are interposed between those two or more components.

II. Exemplary Tissue Dicing Device

FIGS. 1-4 depict an example of a standalone tissue dicing device (2) that is operable to process tissue specimens (24) by cutting the tissue specimens (24) into diced tissue (25). Tissue dicing device (2) of this example comprises a housing (10), a grid cutting element (12), and a dicing chamber (21). A tray (16) is provided below dicing chamber (21). As will be described in greater detail below, grid cutting element (12) is operable to dice tissue in dicing chamber (21), leaving diced tissue (25) on tray (16) for subsequent removal of diced tissue (25) on tray (16). Tissue dicing device (2) further includes a door panel (14), a menu selector (18), and a cutting board (20). As shown in FIG. 1, a coring biopsy needle (22) may be used to deposit tissue specimens (24) on cutting board (20) in dicing chamber (21). Biopsy needle (22) may comprise a conventional coring biopsy needle having an open distal end. For instance, biopsy needle (22) may include a plunger (not shown) that may be retracted to extract a tissue specimen (24)

from a patient and then advanced to deposit the tissue specimen (24) on cutting board (20). Of course, a variety of other types of instruments may be used to harvest tissue specimens (24) from a patient and/or deposit tissue specimens (24) on cutting board (20), including but not limited to various other devices described herein, described in any of the U.S. patents cited herein, described in any of the U.S. patent application Publications cited herein, or described in any of the U.S. Non-Provisional patent applications cited herein.

Grid cutting element (12) of the present example comprises a series of blades (13) that are oriented to form a grid. Of course, blades (13) may be provided in various other arrangements as well (e.g., a series of parallel blades, a pyramidal arrangement, a series of staggered blades, etc.). Blades (13) are fixedly mounted to door panel (14), which is pivotably coupled with housing (10). Each blade (13) has a sharpened edge that is configured to cut through tissue specimens (24). Such sharpened edges may include teeth at various pitches, various other serrated edges, and/or various other configurations. In addition, blades (13) and/or door panel (14) may be configured to allow the density of the blade arrangement to be varied so that tissue specimens (24) may be selectively cut to a particular desired size. Various suitable ways in which tissue dicing device (2) may provide selective variability of the density and/or arrangement of blades (13) will be apparent to those of ordinary skill in the art in view of the teachings herein. Blades (13) may be made from a sheet metal material, such as stainless steel, or any other suitable material or combination of materials.

Figure 2:
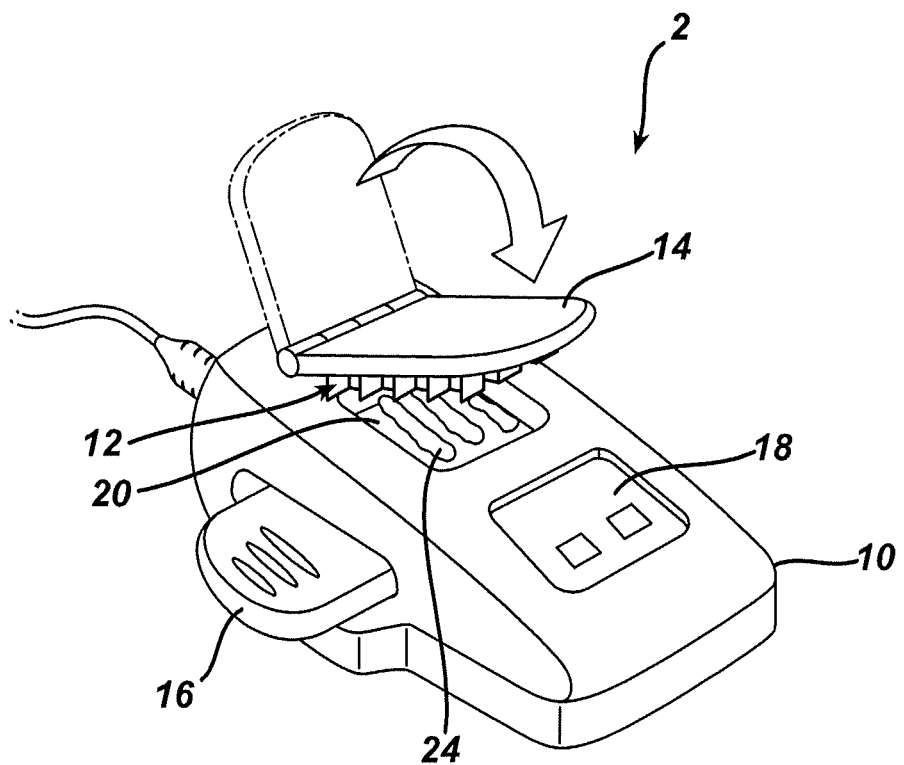
FIG. 2 depicts a perspective view of the tissue dicing device of FIG. 1 in operation.
Figure 3:
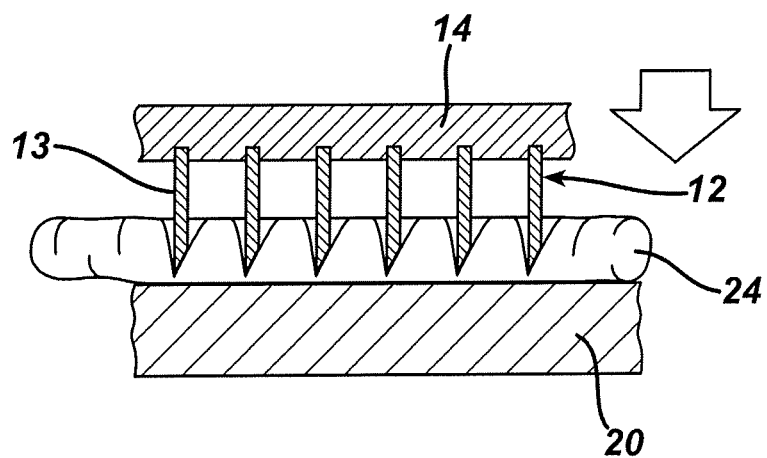
FIG. 3 depicts a side cross-sectional view of a grid cutting element of the tissue dicing device of FIG. 1 in operation.
Figure 4:
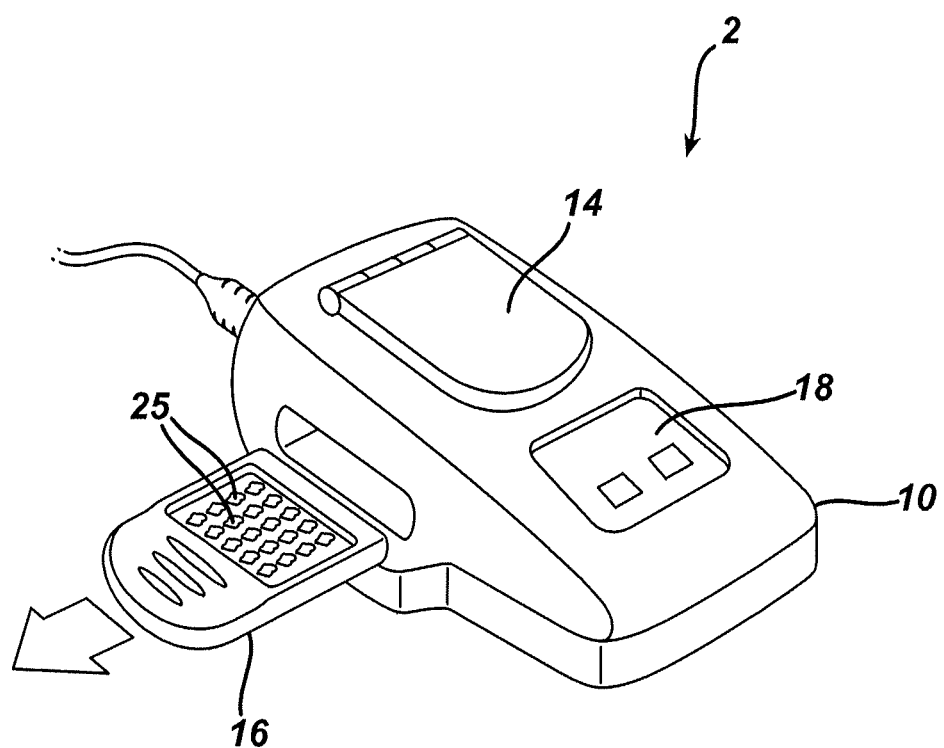
FIG. 4 depicts a perspective view of the tissue dicing device of FIG. 1 with a diced tissue tray removed.

In the present example, cutting board (20) is a removable item that has a smooth surface against which blades (13) cut tissue specimens (24) into diced tissue (25). FIG. 2 shows door panel (14), having grid cutting element (12) attached thereto, pivotably closing onto tissues samples (24) on the cutting board (20). FIG. 3 shows a side view of door panel (14), having grid cutting element (12) attached thereto, closed onto the tissues specimens (24) on cutting board (20), with grid cutting element (12) dicing tissue specimens (24) into diced tissue (25). Cutting board (20) may be manufactured from a material having elastomeric properties and/or various other properties. By way of example only, cutting board (20) may be formed of polyethylene, polypropylene, metal, or wood-based materials, etc. and/or various combinations of materials. In the present example, after tissue specimens (24) are cut into diced tissue (25), cutting board (20) is removed and diced tissue (25) drops onto tray (16), which is located below cutting board (20). As shown in FIG. 4, tray (16) may then be removed from housing (10) and be used to transport diced tissue (25) to another location and/or device for further processing/use. Tray (16) may also be manufactured from a material having elastomeric properties and/or various other properties, including but not limited to polyethylene, polypropylene, metal, or wood-based materials, etc. and/or various combinations of materials.

In some versions, cutting board (20) may slide away into a recess (not shown) within the housing (10) after tissue specimens (24) have been cut into diced tissue (25). When this occurs, diced tissue (25) may be scraped or wiped off cutting board (20) and onto the tray (16) below as cutting board (20) retracts. For instance, diced tissue (25) may be scraped off by a scraper (not shown), a wiper (not shown), or by a wall (not shown) within housing (10) at the perimeter of cutting chamber (21). In addition or in the alternative, cutting board (20) may fold away or flap open like a trap door to allow diced tissue (25) fall onto the tray (16). Various other suitable ways in which diced tissue (25) may be transferred from cutting board (20) to tray (16) will be apparent to those of ordinary skill in the art in view of the teachings herein. It should also be understood that tray (16) itself may be used as a cutting board in some versions, such that a separate cutting board (20) may be omitted. In other words, coring biopsy needle (22) (or some other device) may be used to deposit tissue specimens (24) directly onto tray (16), and blades (13) may cut tissue specimens (24) into diced tissue (25) directly on tray (16).

In the present example, menu selector (18) allows a user to choose from various pre-programmed options. Menu selector (18) may include one or more buttons, switches, displays, and/or various other types of user input/interface features. Options that may be selected from using menu selector (18) may include powering tissue dicing device (2) off and on, selecting the number of times to chop tissue specimens (24) so as to obtain a fine cut diced tissue (25), vary the density of the arrangement of blades (13), and/or otherwise vary the arrangement of blades (13). Other options that may be selected using menu selector (18) will be apparent to those of ordinary skill in the art in view of the teachings herein. It should also be understood that, like other components and features described herein, menu selector (18) may be omitted entirely if desired.

In some merely illustrative variations, grid cutting element (12) is not integrally incorporated into door panel (14). For instance, door panel (14) may instead present a plate (not shown) where grid cutting element (12) would otherwise be located. Cutting element (12) may instead be mounted to housing (10) at a position between the plate of door panel (14) and tray (16), or may be provided in any other suitable location. Tissue specimens (24) may be placed directly on cutting element (12) in some such versions. As the door panel (14) is closed, the plate of door panel (14) may push tissue specimens (24) against the edges of blades (13) of cutting element (12), providing diced tissue (25). Such diced tissue (25) may then drop into tray (16) located below grid cutting element (12). Other suitable components, features, configurations, and operabilities of tissue dicing device (2) will be apparent to those of ordinary skill in the art in view of the teachings herein.

III. Exemplary Tissue Harvesting and Dicing Device

Figure 5:
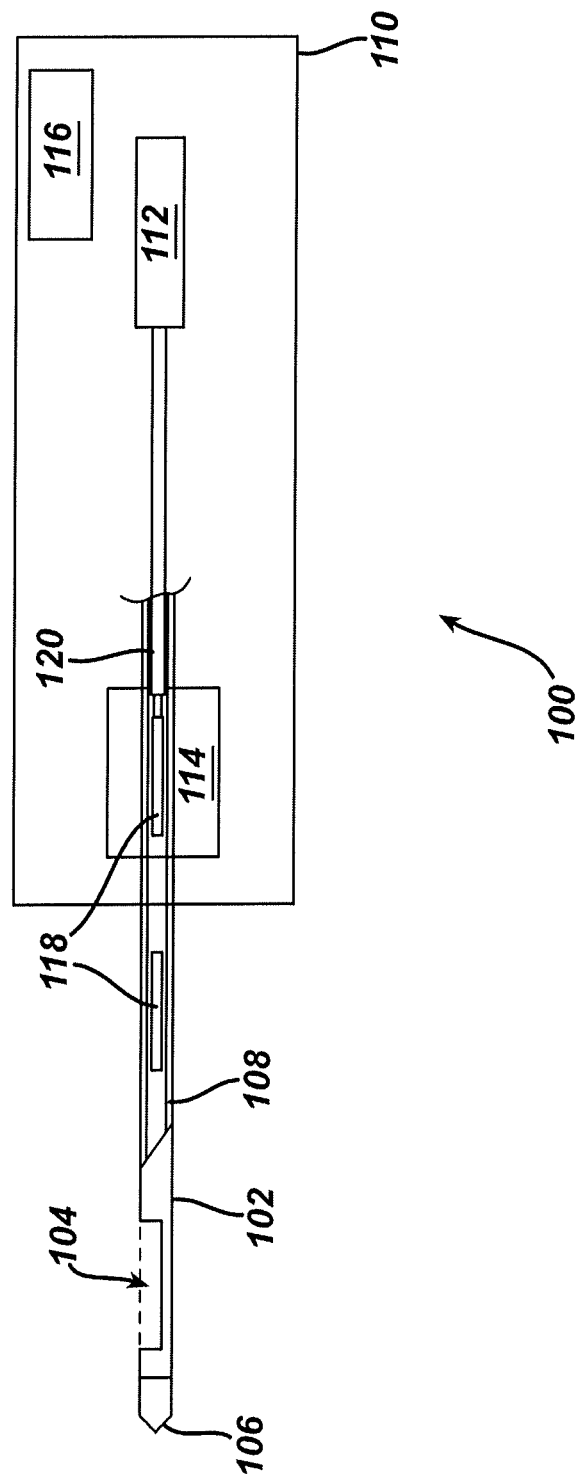
FIG. 5 depicts a system schematic view of an exemplary tissue harvesting device with an integrated dicing mechanism.

While tissue dicing device (2) of FIGS. 1-4 is a stand-alone device that is separate from the device used to harvest tissue specimens (24), it should be understood that tissue dicing capabilities may be incorporated as an integral feature of a tissue harvesting device. For instance, FIG. 5 depicts an exemplary tissue harvesting device (100) having an integral tissue dicing mechanism (114). As shown in FIG. 5, tissue harvesting device (100) of this example comprises a needle (102) and a tissue collection body (110). Needle (100) of this example has a closed, tissue piercing tip (106) and a side aperture (104) located proximal to tip (106). An inner cutter (108) is slidably and rotatably positioned within needle (100) and may be rotated and advanced distally within needle (100) to sever tissue protruding through side aperture (104) when needle (100) is inserted in a patient. Tissue collection body (110) includes a cutter actuation mechanism (116), a vacuum source (112), a tubular knock out pin (120), and a dicing mechanism (114). FIG. 5 also shows a tissue specimen (118) as it moves through tissue harvesting device (100). Tubular knock out pin (120) is positioned coaxially within inner cutter (108), and is configured to maintain a substantially constant position relative to tissue collection body (110) even while inner cutter (108) moves relative to tissue collection body (110). Knock out pin (120) is positioned adjacent to dicing mechanism (114), and is configured to push tissue specimen (118) out through the open distal end of inner cutter (108) into dicing mechanism (114) as inner cutter (108) is retracted proximally relative to knock out pin (120). Dicing mechanism (114) may be configured in accordance with the various teachings of tissue dicing mechanisms herein.

Cutter actuation mechanism (116) is operable to selectively advance and retract inner cutter (108) relative to tissue collection body (110), and may be configured in accordance with the teachings of any U.S. patent, U.S. patent application Publication, or U.S. Non-Provisional patent application cited herein; or may have any other suitable configuration. Vacuum source (112) is operable to draw a vacuum through needle (102). Such a vacuum may assist in drawing tissue into side aperture (104). Vacuum source (112) may also be operable to draw a vacuum through cutter (108), which may assist in carrying tissue specimen (118) proximally relative to needle (102). While vacuum source (112) is shown as being an integral component of tissue collection body (110), it should be understood that vacuum source (112) may instead be located external to tissue collection body (110). For instance, vacuum source (112) may be coupled with needle (102) and/or some other component of tissue harvesting device (100) via one or more conduits, etc.

In an example of operating tissue harvesting device (100), an operator may insert needle (102) into a patient at any suitable location (e.g., in the patient's thigh muscle). Inner cutter (108) may be located at a distal position, effectively "closing off" side aperture (104) during such insertion. Inner cutter (108) is then retracted upon sufficient insertion of needle (102) and vacuum source (112) is activated to draw tissue into side aperture (104). Inner cutter (108) is then advanced distally past side aperture (104) to sever tissue specimen (118) from tissue protruding through side aperture (104). Tissue specimen (118) is then positioned inside of inner cutter (108). Inner cutter (108) is then retracted proximally Tissue specimen (118) moves proximally with cutter until tissue specimen (118) engages knock out pin (120). Inner cutter (108) continues to retract as tissue specimen (118) engages knock out pin (120), such that knock out pin (120) eventually pushes tissue specimen (118) out through the open distal end of inner cutter (108). Tissue specimen (118) then drops into dicing mechanism (114). As will be described in greater detail below, dicing mechanism (114) then dices tissue specimen (118).

It should be understood from the foregoing that at least part of tissue harvesting device (100) may be constructed like a conventional biopsy device that would be used for excising soft tissue specimens. By way of example only, at least part of tissue harvesting device (100) may be constructed in accordance with the teachings of U.S. Pat. No. 5,526,822, entitled "Method and Apparatus for Automated Biopsy and Collection of Soft Tissue," issued Jun. 18, 1996, the disclosure of which is incorporated by reference herein; U.S. Pat. No. 6,086,544, entitled "Control Apparatus for an Automated Surgical Biopsy Device," issued Jul. 11, 2000, the disclosure of which is incorporated by reference herein; and/or U.S. Pub. No. 2008/0214955, entitled "Presentation of Biopsy Sample by Biopsy Device," published Sep. 4, 2008, the disclosure of which is incorporated by reference herein. For instance, FIGS. 6A-6H of U.S. Pat. No. 5,526,822 show the cooperation between a closed-end needle with side aperture and a hollow tubular cutter with sharp open end within the needle. FIGS. 6E-6H of U.S. Pat. No. 5,526,822 also show how a stationary "knock out pin" pushes severed tissue out the open distal end of the cutter when the cutter is retracted proximally.

U.S. Pat. No. 6,086,544 also discloses a combination of an outer needle with a side aperture and an inner cutter, as well as a knock out pin (referred to as a "tissue remover") for pushing severed tissue out of the open distal end of the inner cutter. Similarly, U.S. Pub. No. 2008/0214955 discloses a needle with side aperture and an inner cutter. However, instead of a knockout pin, the severed tissue is pulled proximally through the inner cutter using a vacuum. It should therefore be understood that some variations of tissue harvesting device (100) may include proximal communication of tissue specimens (118) through inner cutter (108) to a tissue dicing mechanism (114) without a knock out pin (120) being included. In other words, a biopsy device like one taught in U.S. Pub. No. 2008/0214955 may have its tissue sample holder modified to provide a tissue dicing mechanism (114). Various suitable ways in which a tissue sample holder of an otherwise conventional biopsy device may be modified to provide an integral tissue dicing mechanism (114) will be apparent to those of ordinary skill in the art in view of the teachings herein.

Figure 6:
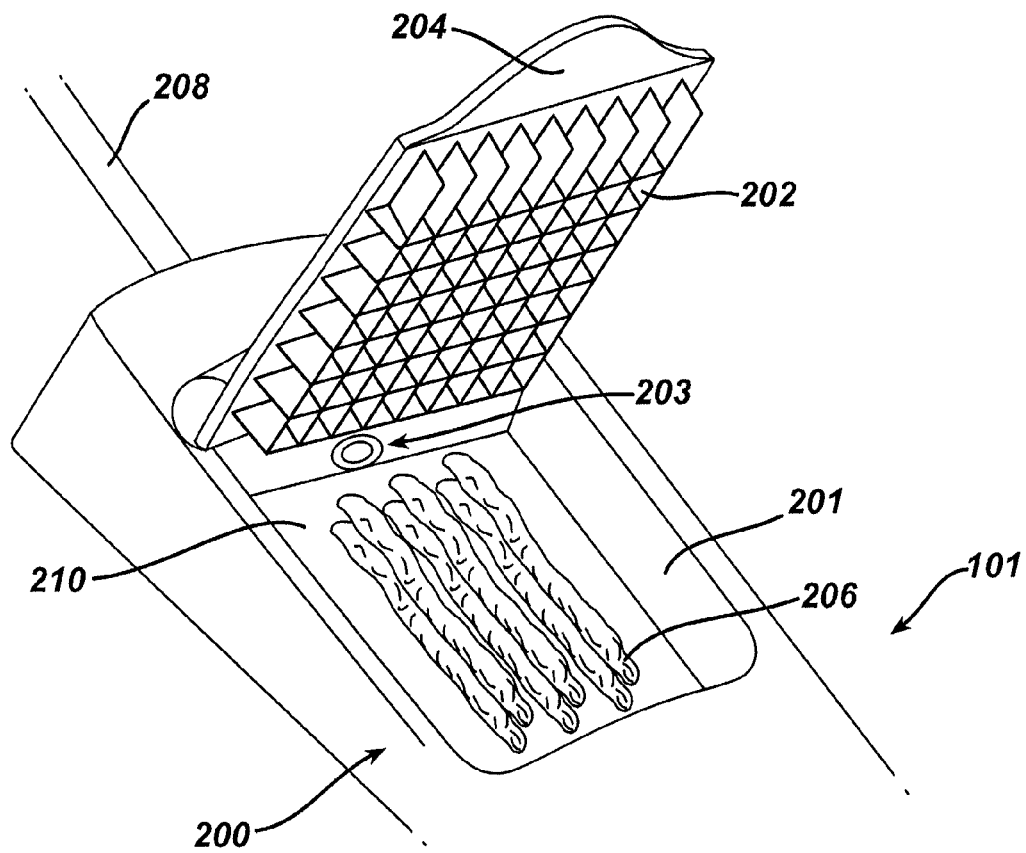
FIG. 6 depicts a partial perspective view of an exemplary tissue harvesting device with an integrated dicing mechanism.
Figure 7:
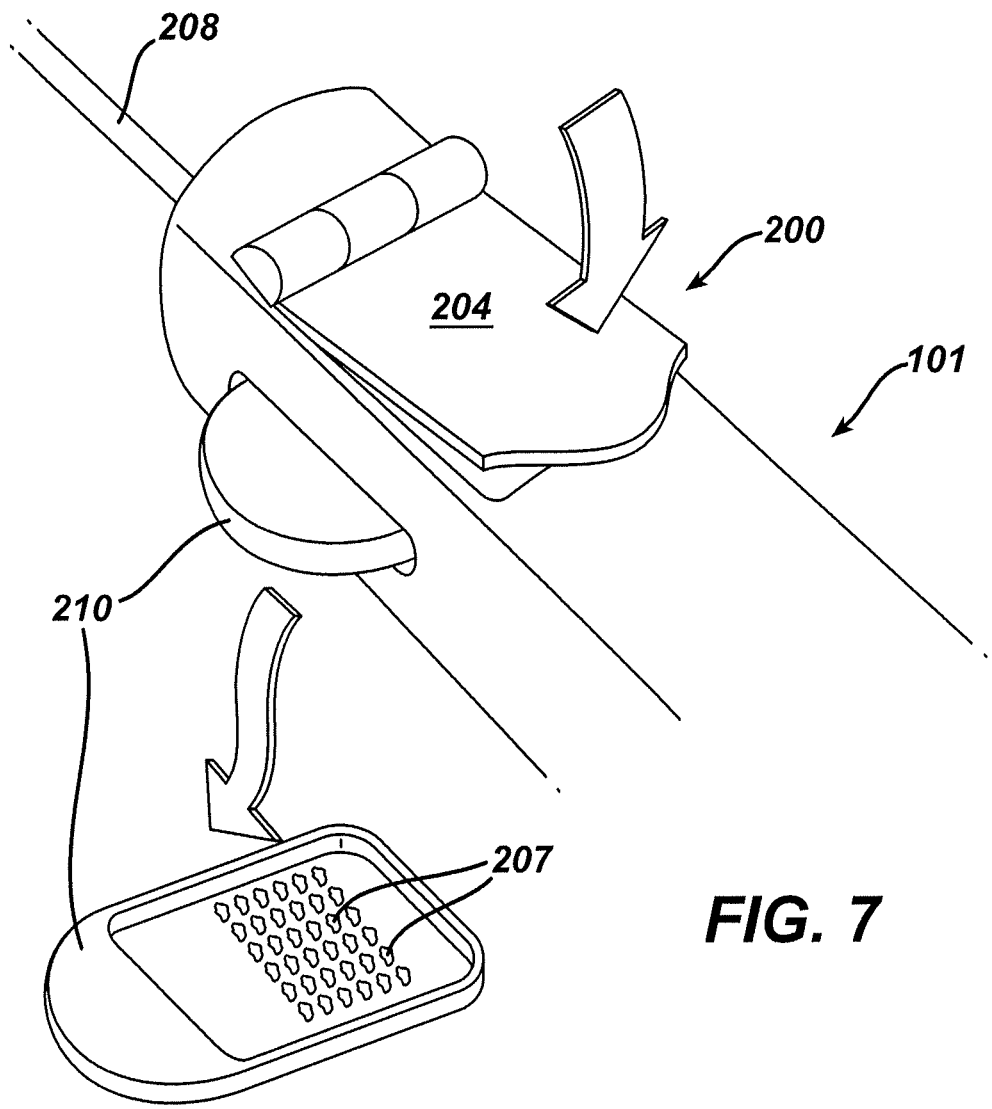
FIG. 7 depicts a partial perspective view of the tissue harvesting device of FIG. 6 in operation.

FIGS. 6-7 show a merely illustrative example of how a tissue dicing mechanism (200) may be incorporated into a tissue harvesting device (101). In this example, tissue harvesting device (101) includes a needle (208), like needle (102) described above. Tissue harvesting device (101) also includes a cutter (not shown), like inner cutter (108) described above. As shown in FIG. 6-7 tissue dicing mechanism (200) is located proximal to needle (102). As best seen in FIG. 6, tissue dicing mechanism (200) includes a cutting chamber (201). An opening (203) provides communication of tissue specimens (206) into cutting chamber (201). In particular, the inner cutter (not shown) may be advanced distally into opening (203) to reach needle (208), and may be retracted proximally through opening (203) and cutting chamber (201) during a cutting stroke by the cutter. A knock out pin (not shown) may be positioned at the proximal end of cutting chamber (201) to push tissue specimens (206) out the distal end of the cutter, such that the tissue specimens (206) are deposited in cutting chamber (201).

Dicing mechanism (200) of the present example comprises cutting chamber (201), a grid cutting element (202), a door panel (204), and tissue tray (210). Grid cutting element (202) and door panel (204) of this example are configured and operable in a manner similar to grid cutting element (12) and door panel (14), respectively, described above. Tissue tray (210) of this example is configured and operable as essentially a combination of cutting board (20) and tray (16) described above. Accordingly, door panel (204) with grid cutting element (202) is closed as shown in FIG. 7 to dice tissue specimens (206) by cutting tissue specimens (206) against tissue tray (210). After tissue specimens (206) have been diced, tissue tray (210) is removed from tissue harvesting device (101) for transport and/or further processing of diced tissue (207).

In some other versions, dicing mechanism (200) is located further proximally in tissue harvesting device (101), with the inner cutter that translates through needle (208) being located entirely distal to dicing mechanism (200). In some such versions, a conduit (not shown) provides communication from the proximal end of the inner cutter to cutting chamber (201). For instance, a vacuum source may be in fluid communication with cutting chamber (201), and a vacuum induced by the vacuum source may be communicated to the hollow interior of the cutter via cutting chamber (201) and via the conduit that couples the inner cutter with cutting chamber (201). When the cutter is advanced distally relative to needle (208) to sever a tissue specimen (206), this vacuum in the cutter, in the conduit, and in cutting chamber (201) may pull the severed tissue specimen (206) proximally through the cutter and through the conduit to reach cutting chamber (201). A filter or other feature may prevent the tissue specimen (206) from travelling further than cutting chamber (201), such that the tissue specimen (206) is deposited in cutting chamber (201). Cutting element (202) may then be used to dice one or more tissue specimens (206) in cutting chamber (201). In some such versions, door panel (204) is closed and provides a seal while tissue specimens (206) are harvested, to maintain the vacuum during harvesting of tissue specimens (206). Similarly, tray (210) is in a sealed yet removable engagement with tissue harvesting device (101) to maintain the vacuum during harvesting of tissue specimens (206). It should be understood that the cutting action by cutting element (202) may require more than simply closing door panel (204) in some such versions, particularly those where door panel (204) must be closed in order to maintain a sufficient vacuum during the process of harvesting tissue specimens (206). For instance, an actuation mechanism may be provided to selectively actuate cutting element (202) after door panel (204) is closed, with such an actuation mechanism providing sufficient clearance for tissue specimens (206) to be deposited under cutting element (202) before a dicing process is to be initiated. Various suitable ways in which such versions of tissue harvesting device (101) may be configured will be apparent to those of ordinary skill in the art in view of the teachings herein.

IV. Exemplary Fistula Plug Preparation System

FIGS. 8-13 depict an exemplary fistula plug preparation system (400). In the present example, fistula plug preparation system (400) is operable to provide a plug for use in surgery to treat a fistula or other type of anatomical defect, etc. For instance, the plug may be sized and configured for delivery into a variety of fistula tracts. The plug generally comprises a scaffold material (404) formed into a narrow cylindrical shape that is configured for insertion into a fistula with a cell matrix. Scaffold material (404) may comprise a biocompatible material that may be formed from a natural material, a synthetic material, a bioabsorbable polymer, a non-woven polymer, other types of polymers, and/or other types of materials or combinations of materials. Examples of suitable biocompatible materials include starch, chitosan, cellulose, agarose, amylose, lignin, hyaluronan, alginate, polyhydroxybutyrate (PHB), poly (hyaluronic acid), poly(vinyl pyrrolidone) (PVP), polylactide (PLA), polyglycolide (PGA), polycaprolactone (PCL), and their copolymers, non-woven VICRYL® (Ethicon, Inc., Somerville, N.J.), MONOCRYL material, fibrin, non-woven poly-L-lactide, and non-woven PANACRYL (Ethicon, Inc., Somerville, N.J.), and/or any other suitable material or combination of materials. It should also be understood that scaffold material (404) may include any one or more of the various medical fluid components referred to herein. Other suitable materials will be apparent to those of ordinary skill in the art in view of the teachings herein.

As will be described in greater detail below, a plug formed of scaffold material (404) may be inserted into a fistula by a catheter (412), and may be flushed with a cell matrix to therapeutically address the fistula. Such a cell matrix may be formed at least in part by tissue that was harvested from the same patient that has the fistula (and/or tissue harvested from some other source or sources). For instance, at least some of the cells in the cell matrix may be isolated or derived in part from such harvested tissue. The cells may include, for example, genetically engineered cells, precursor cells, progenitor cells, precursor cells, stem cells, bone marrow cells, umbilical cord blood cells, angioblasts, endothelial cells, osteoblasts, smooth muscle cells, kidney cells, fibroblasts, myofibroblasts, cardiovascular cells, neural cells, neural precursor cells, amniotic cells and post-partum placental cells, any other type of cells referred to herein, and/or any other suitable types of cells, including combinations of different kinds of cells. The harvested tissue may have been diced using any of the tissue dicing devices (2, 114, 200) described herein and/or may have been processed in any other suitable fashion before being introduced to scaffold material (404). While the cell matrix is introduced to a plug formed by scaffold material (404) after the plug has been inserted in a fistula or as the plug is being inserted in a fistula in the present example, it should be understood that the cell matrix may alternatively be introduced to scaffold material (404) before or during the process in which scaffold material (404) is formed into a plug or at any other suitable time.

Figure 8:
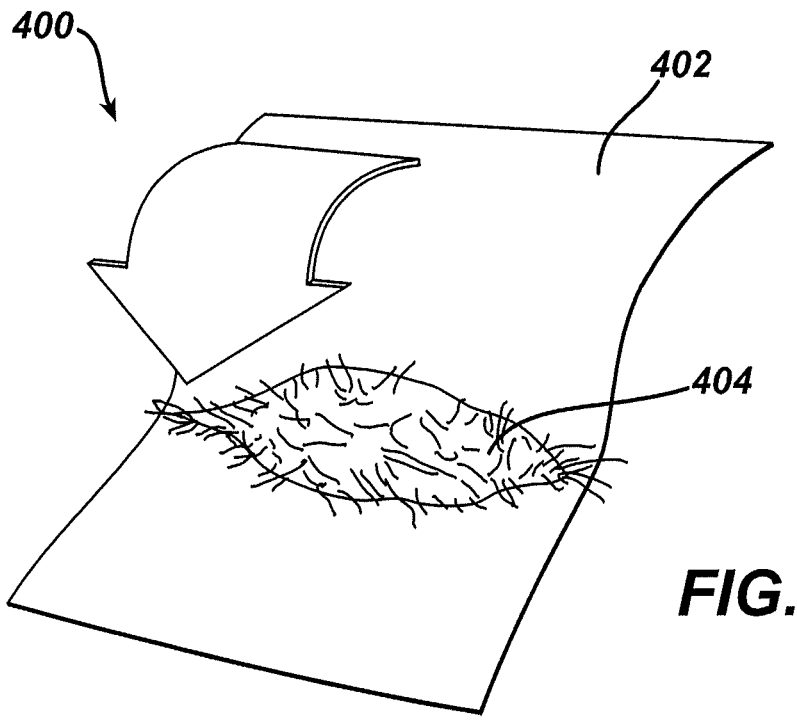
FIG. 8 depicts a perspective view of an exemplary self-expanding fistula plug creation and delivery system, shown in a first stage of an exemplary process.
Figure 9:
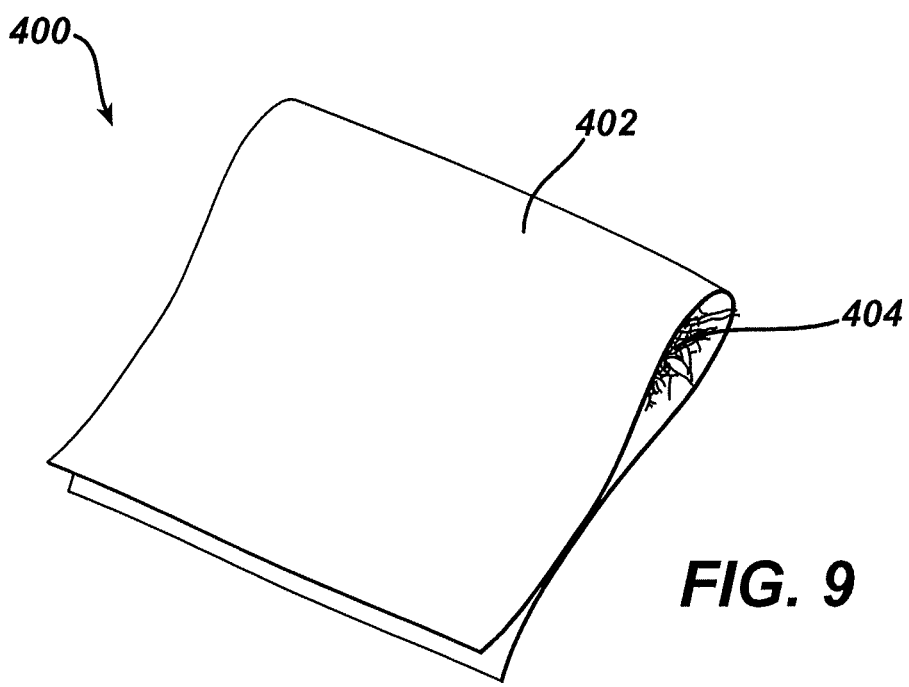
FIG. 9 depicts a perspective view of the self-expanding fistula plug creation and delivery system of FIG. 8, shown in a second stage of the process.

Fistula plug preparation system (400) of this example comprises a wrapper (402), a slotted plate (416), a forming device (406), a plunger (408), and a catheter (412). Wrapper (402) generally comprises a thin foldable sheet operable to receive scaffold material (404). Wrapper (402) may be formed at least in part of a generally non-stick material or materials (e.g., silicone, ultra high molecular weight polyethylene, a coating of polytetrafluoroethylene (PTFE), etc.) that is configured to prevent scaffold material (404) from sticking to wrapper (402), even if wrapper (402) is folded over itself with scaffold material (404) contained therein. Wrapper (402) is configured to transition from a flat position as shown in FIG. 8 to a folded position as shown in FIG. 9. However, any suitable position for wrapper (402) may be used to enclose scaffold material (404).

Figure 10:
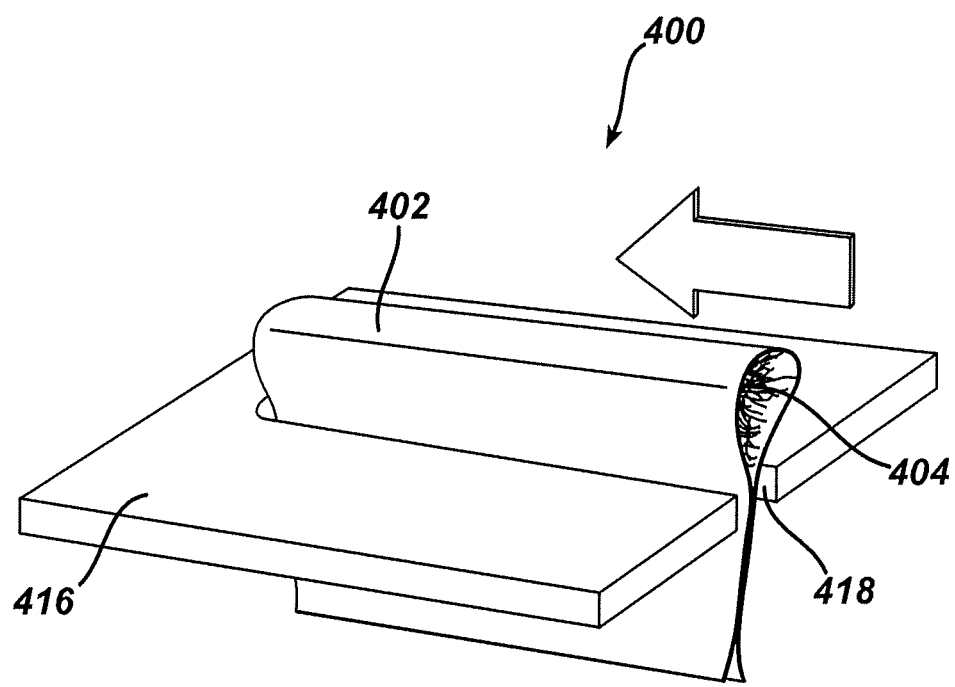
FIG. 10 depicts a perspective view the self-expanding fistula plug creation and delivery system of FIG. 8, shown in a third stage of the process.

Slotted plate (416) comprises a generally flat and rectangular plate. However, it should be understood that slotted plate (416) may have any other suitable shape, configuration, or size. Slotted plate (416) defines a slot (418) extending through slotted plate (416). Slot (418) extends along almost the entire length of slotted plate (416) such that a portion of slotted plate (416) still connects what would otherwise be two separate portions of slotted plate (416). As shown in FIG. 10, folded wrapper (402) containing scaffold material (404) may be inserted into slot (418) of slotted plate (416), such that the length of wrapper (402) containing scaffold material (404) may extend for at least part of the length of slot (418). Furthermore, slot (418) is sufficiently narrow so as to prevent scaffold material (404) from inadvertently falling out of wrapper (402) thought slot (418). At this stage, wrapper (402) may be pulled downwardly relative to slotted plate (416). It should be understood that such pulling may allow wrapper (402) to compress scaffold material (404) by bearing against slotted plate (416). In addition or in the alternative, opposite ends of wrapper (402) may be alternatingly pulled down in a rocking fashion to roll scaffold material (404) within wrapper (402).

Figure 11:
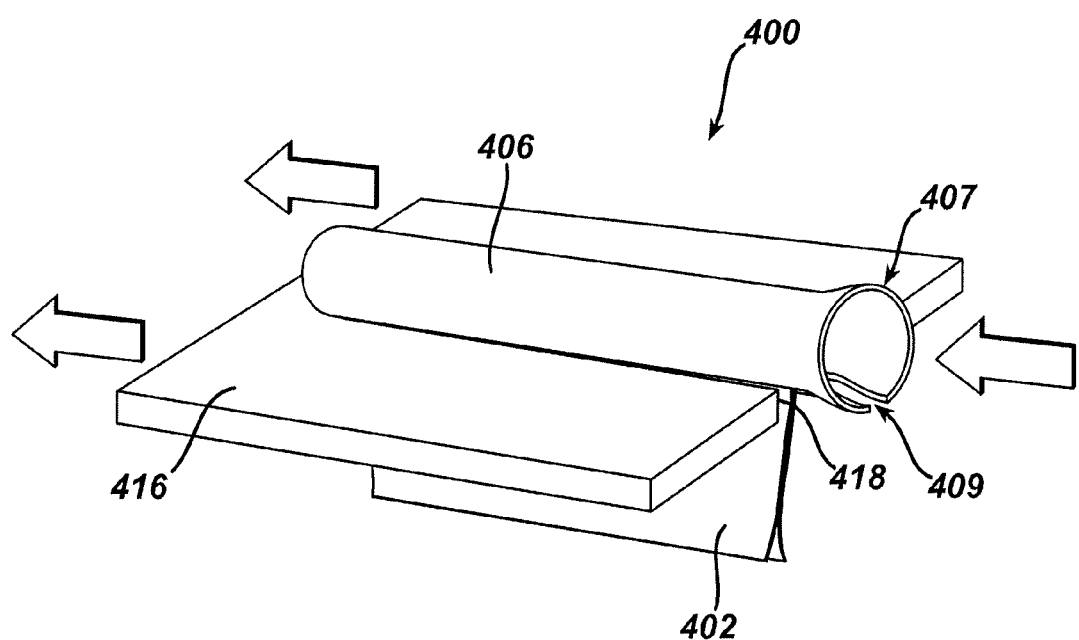
FIG. 11 depicts a perspective view of the self-expanding fistula plug creation and delivery system of FIG. 8, shown in a fourth stage of the process.

As shown in FIG. 11, forming device (406) comprises a cylindrical tube having a flared end (407). While wrapper (402) is substantially flexible in the present example, forming device (406) is substantially rigid (e.g., formed of steel, rigid plastic, etc.) in the present example. Forming device (406) further comprises a slot (409) extending along the full length of forming device (406). Slot (409) is configured to allow wrapper (402) containing scaffold material (404) to fit within forming device (406) such that at least a portion of wrapper (402) extends though slot (409) of forming device (406) in addition to extending through slot (418) of slotted plate (416). Flared end (407) of forming device (406) is configured to allow easy insertion of wrapper (402) containing scaffold material (404) into forming device (406). Furthermore, the inner diameter of forming device (406) may be smaller than the outer diameter of wrapper (402) containing scaffold material (404), such that once forming device (406) is placed over wrapper (402) containing scaffold material (404), wrapper (402) containing scaffold material (404) is compressed to form a generally cylindrical shape. Of course, forming device (406) may be any other suitable shape, and may be configured to form scaffold material (404) into any other suitable shape.

Figure 12:
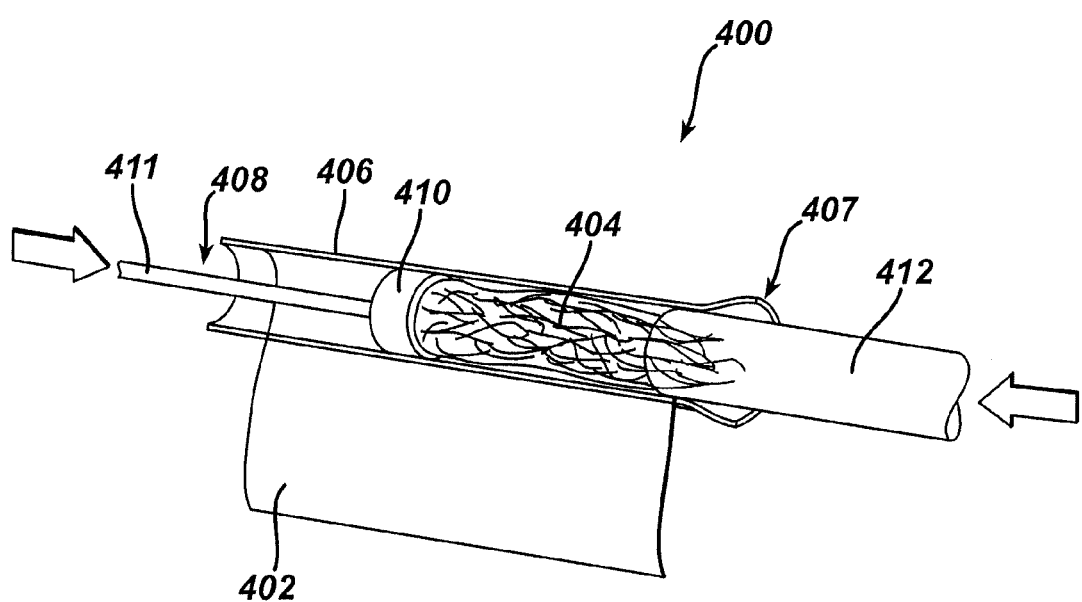
FIG. 12 depicts a perspective view of the self-expanding fistula plug creation and delivery system of FIG. 8, shown in a fifth stage of the process.
Figure 13:
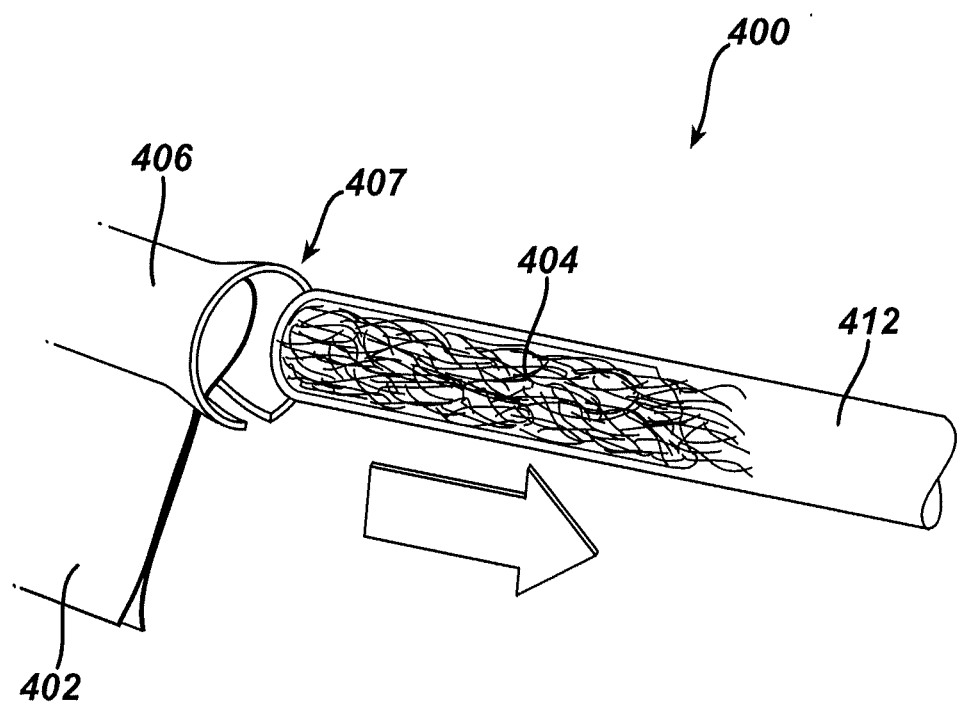
FIG. 13 depicts a perspective view of the self-expanding fistula plug creation and delivery system of FIG. 8, shown in a sixth stage of the process.

As shown in FIGS. 12-13, scaffold material (404) that has been formed into a cylindrical shape may be inserted into catheter (412). Catheter (412) of the present example has a generally cylindrical shape, though it should be understood that any other suitable shape may be used. Catheter (412) may be positioned at flared end (407) of forming device (406) for receipt of scaffold material (404). Removal plunger (408), which comprises an elongate shaft (411) having a piston-like head (410), may then be inserted into the opposite end of forming device (406) to urge scaffold material (404) out of forming device (406) and out of wrapper (402), into catheter (412). Thus, removal plunger (408) may be used to push scaffold material (404) into catheter (412) from forming device (406). Once scaffold material (404) is removed from forming device (406) and placed in catheter (412), catheter (412) with scaffold material (404) may be removed and used immediately or stored for later use.

When catheter (412) is ready for use to deploy scaffold material (404), catheter (412) may be inserted in a fistula tract and then scaffold material (404) may be ejected as a plug into the fistula. To the extent that a cell matrix had not yet been introduced to scaffold material (404) at this stage, the cell matrix or slurry may be communicated through catheter (412) or in some other way to impregnate scaffold material (404) as catheter (412) is being withdrawn from the fistula to leave impregnated scaffold material (404) within the fistula. The impregnated scaffold material (404) may thus be deployed within the fistula in a manner similar to that by which a self-expanding stent is deployed. Of course, scaffold material (404) may alternatively be deployed in any other suitable fashion. Still other suitable features, components, configurations, functionalities, and operabilities that may be provided by fistula plug preparation system (400) will be apparent to those of ordinary skill in the art in view of the teachings herein. Similarly, various other suitable ways in which fistula plug preparation system (400) may be used will be apparent to those of ordinary skill in the art in view of the teachings herein.

V. Miscellaneous

While several devices and components thereof have been discussed in detail above, it should be understood that the components, features, configurations, and methods of using the devices discussed are not limited to the contexts provided above. In particular, components, features, configurations, and methods of use described in the context of one of the devices may be incorporated into any of the other devices. Furthermore, not limited to the further description provided below, additional and alternative suitable components, features, configurations, and methods of using the devices, as well as various ways in which the teachings herein may be combined and interchanged, will be apparent to those of ordinary skill in the art in view of the teachings herein.

Versions of the devices described above may be actuated mechanically or electromechanically (e.g., using one or more electrical motors, solenoids, etc.). However, other actuation modes may be suitable as well including but not limited to pneumatic and/or hydraulic actuation, etc. Various suitable ways in which such alternative forms of actuation may be provided in a device as described above will be apparent to those of ordinary skill in the art in view of the teachings herein.

Versions of the devices described above may have various types of construction. By way of example only, any of the devices described herein, or components thereof, may be constructed from suitable metals, ceramics, plastics, or combinations thereof. Furthermore, although not required, the construction of devices described herein may be configured to be compatible with or optimize their use with various imaging technologies. For instance, a device configured for use with MRI may be constructed from all non-ferromagnetic materials. Also for instance, when using optional imaging technologies with devices described herein, certain configurations may include modifications to materials of construction such that portions or the device may readily appear in a resultant image. Various suitable ways in which these and other modifications to the construction of devices described herein may be carried out will be apparent to those of ordinary skill in the art in view of the teachings herein.

Versions of the devices described above may have application in conventional medical treatments and procedures conducted by a medical professional, as well as application in robotic-assisted medical treatments and procedures.

Versions of described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A tissue processing device comprising:
   (a) a housing;
   (b) a cutting element;

(c) a cutting chamber, wherein the cutting chamber is formed in the top of the housing, wherein the cutting chamber has a base, and wherein the cutting element is operable to dice tissue in the cutting chamber;

(d) a tissue tray, wherein the tissue tray is configured to receive tissue diced within the cutting chamber;

(e) a tray recess, wherein the tray recess is formed in a side of the housing at the base of the cutting chamber, wherein the tray recess is substantially parallel with the base of the cutting chamber, wherein the tray recess is in fluid communication with the cutting chamber, and wherein the tray recess is configured to slidably receive the tissue tray; and (f) a door panel, wherein the door panel is hingedly attached to the housing, wherein the door panel is configured to cover the cutting chamber when in a closed state, wherein the cutting element is integral with the door panel, and wherein the cutting element is configured to contact the tissue tray when the door panel is in the closed state.

2. The device of claim 1, further comprising a user input feature, wherein the user input feature is operable to reconfigure the cutting element.

3. The tissue processing device of claim 2, wherein the user input feature is further operable to establish the number of times a tissue sample is to be diced.

4. The tissue processing device of claim 1, wherein the cutting element comprises a plurality of blades.

5. The tissue processing device of claim 4, wherein the blades of the plurality of blades are oriented to form a grid pattern.

6. The tissue processing device of claim 1, further comprising a cutting board, wherein the cutting board is configured to receive tissue diced within the cutting chamber.

7. The tissue processing device of claim 6, wherein the cutting board is removably disposed within the cutting chamber.

8. The tissue processing device of claim 6, wherein the cutting element is configured to contact the cutting board when the door panel is in the closed state.

9. The tissue processing device of claim 6, wherein the cutting board is defined by the tissue tray.

10. The tissue processing device of claim 6, wherein the housing comprises a cutting board recess.

11. The tissue processing device of claim 10, wherein the cutting board recess is configured to receive the cutting board, and wherein the cutting board recess is further configured to remove diced tissue from the cutting board upon entry into the cutting board recess.

12. The tissue processing device of claim 6, wherein the cutting board comprises a plurality of sections, and wherein at least one of the sections of the plurality of sections is hingedly attached to an interior surface of the cutting chamber.

13. The tissue processing device of claim 1, wherein the cutting element is mounted within the cutting chamber.

14. A tissue processing device comprising:

(a) a housing;

(b) a cutting element;

(c) a cutting chamber, wherein the cutting chamber is formed in the top of the housing, wherein the cutting chamber has a base, and wherein the cutting element is operable to dice tissue in the cutting chamber;

(d) a door panel, wherein the door panel is hingedly attached to the housing, and wherein the door panel is configured to cover the cutting chamber when in a closed state, wherein the door panel further comprises a cutting surface, wherein the cutting surface is configured to contact the cutting element when the door panel is in the closed state;

(e) a tissue tray, wherein the tissue tray is configured to receive tissue diced within the cutting chamber; and (f) a tray recess, wherein the tray recess is formed in a side of the housing at the base of the cutting chamber, wherein the tray recess is in fluid communication with the cutting chamber, and wherein the tray recess is configured to slidably receive the tissue tray.

15. The tissue processing device of claim 14, wherein the tissue processing device further comprises a user input feature, wherein the user input feature is operable to perform one or both of the functions of reconfiguring the cutting element or establishing the number of times a tissue sample is to be diced.

16. A method of processing tissue, the method comprising:

(a) depositing a tissue specimen in a tissue dicing chamber;

(b) closing a door panel over the tissue dicing chamber, wherein the act of closing the door panel over the tissue dicing chamber causes the tissue specimen to engage a grid cutting element;

(c) dicing the tissue specimen with the grid cutting element to provide diced tissue;

(d) catching the diced tissue within a tissue tray; and (e) removing the tissue tray from the tissue dicing chamber.

17. The method of claim 16, further comprising the step of removing a cutting board.

* * * * *